United States Patent [19]

Torii et al.

[11] Patent Number: 5,656,755
[45] Date of Patent: Aug. 12, 1997

[54] PROCESS FOR PREPARATION ON 3-SUBSTITUTED CEPHEM COMPOUND

[75] Inventors: Shigeru Torii, Akaiwa-gun; Hideo Tanaka, Okayama; Michio Sasaoka; Takashi Shiroi, both of Itano-gun, all of Japan

[73] Assignee: Otsuka Kagaku Kabushiki Kaisha, Osaka, Japan

[21] Appl. No.: 464,853

[22] PCT Filed: Nov. 4, 1994

[86] PCT No.: PCT/JP94/01859

§ 371 Date: Jul. 6, 1995

§ 102(e) Date: Jul. 6, 1995

[87] PCT Pub. No.: WO95/13281

PCT Pub. Date: May 18, 1995

[30] Foreign Application Priority Data

Sep. 11, 1993 [JP] Japan ................................. 5-279311

[51] Int. Cl.$^6$ ................................. C07D 501/36
[52] U.S. Cl. ..................... 540/230; 540/215; 540/222
[58] Field of Search ..................... 540/230, 215, 540/222

[56] References Cited

U.S. PATENT DOCUMENTS 5,266,691  11/1993  Farino et al. ........................ 540/230

OTHER PUBLICATIONS

Journal of the Chemical Society, Chemical Comm., No. 12, 21 Jun. 1994; Tanaka et al., pp. 1461–1462.
Cram & Hammond, "Organic Chemistry" 2nd Edition 1962, pp. 565–567.

*Primary Examiner*—Mukund J. Shah
*Assistant Examiner*—Pavanaram K. Sripada

[57] ABSTRACT

An object of the invention is to provide a process for preparing a 3-substituted cephem compound from an allenyl-β-lactam compound which can be easily produced from an inexpensive penicillin compound by a simple reaction procedure.

The process of the invention comprises reacting an allenyl-β-lactam compound with an organohalogen compound in the presence of a metal having a standard oxidation-reduction potential of −0.3 (V/SCE) or less in an amount at least equimolar with the allenyl-β-lactam compound and 0.0001 to 0.5 mole, per mole of the allenyl-β-lactam compound, of a metal compound having a higher standard oxidation-reduction potential than said metal.

7 Claims, No Drawings

PROCESS FOR PREPARATION ON 3-SUBSTITUTED CEPHEM COMPOUND

TECHNICAL FIELD

The present invention relates to a process for preparing a 3-substituted cephem compound from an allenyl-β-lactam compound which can be easily produced from an inexpensive penicillin compound by a simple reaction procedure.

The 3-substituted cephem compound prepared by the process of the present invention is useful as an antibacterial agent having a wide antibacterial spectrum (e.g., Japanese Unexamined Patent Publications Nos. 119593/1973, 37788/1986, 51688/1987, 211287/1988 and 313482/1989).

TECHNICAL BACKGROUND

Japanese Unexamined Patent Publication No.119593/1973 discloses a process for preparing a 3-substituted cephem compound by coupling a carbonyl compound with a 3-phosphoranilideneethyl cephalosporin compound derived from a 3-halogenomethyl cephalosporin compound.

Japanese Unexamined Patent Publication No.37788/1986 and. Helv. Chim. Acta, 57, 2024 (1974) disclose processes for preparing a 3-substituted arylmethyl cephem compound by coupling a 3-acetoxymethyl cephalosporin compound with a substituted benzene in the presence of a Lewis acid.

A typical process for preparing the 3-substituted cephem compound was reported which comprises subjecting to coupling reaction a 3-trifluorooxycephem (A) or a 3-chloromethylcephem (B) and an organotin compound in the presence of a palladium catalyst as illustrated below in a reaction scheme (J. Org. Chem., 55, 5833–5847, 1990):

comprises reacting an allenyl-β-lactam compound represented by the formula

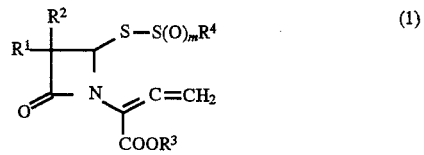

wherein $R^1$ is a hydrogen atom, a halogen atom, an amino group or a protected amine group, $R^2$ is a hydrogen atom, a halogen atom, a lower alkoxy group, a lower acyl group, a lower alkyl group, a lower alkyl group having a hydroxyl group or a protected hydroxyl group as a substituent, a hydroxyl group or a protected hydroxyl group, $R^3$ is a hydrogen atom, or a carboxylic acid-protecting group, $R^4$ is an aryl group optionally having a substituent or a nitrogen-containing aromatic heterocyclic group optionally having a substituent, and m is 0 or 2, namely the starting material used in the process of the invention, with a nucleophile represented by the formula wherein Y is a nucleophile residue, giving a 3-substituted cephem compound represented by the formula

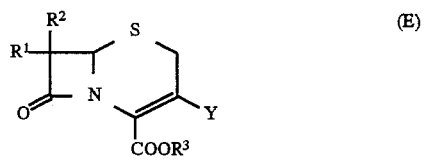

wherein $R^1$, $R^2$, $R^3$ and Y are as defined above (Japanese Unexamined Patent Publication No.282387/1992). This process, however, can not produce the contemplated com-

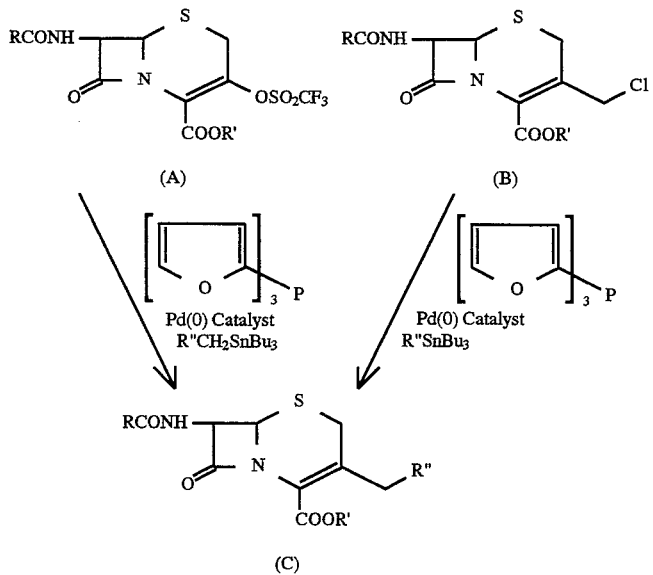

However, the foregoing known processes all require an expensive starting material having a cephalosporin skeleton. The process shown above in the reaction scheme has the drawback, from a commercial viewpoint, of using a theoretical amount of a detrimental organotin compound and an expensive palladium catalyst.

On the other hand, attempts have been made to prepare a 3-substituted cephem compound from an inexpensive penicillin derivative. For example, a process is known which pound of the present invention because the compound of the formula (D) wherein Y is an alkenylmethyl group or arylmethyl group can not act as a nucleophile. The aforesaid publication teaches nothing about some features of the present invention such as the use of a specific metallic reducing agent and a specific organohalogen compound.

A technique for preparing a compound having a β-lactam ring is disclosed, for example, in Japanese Unexamined Patent Publication No.211055/1992, the technique using lead, copper, titanium, bismuth, antimony or the like as a metallic reducing agent along with a metal such as aluminum, zinc, magnesium, tin or the like which have a higher ionization tendency than said metallic reducing agent. Stated more specifically, the publication discloses a process comprising reacting a halogenated β-lactam compound represented by the formula

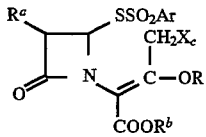

wherein $R^a$ is an amino group or a protected amino group, $R^b$ is a hydrogen atom or a carboxyl-protecting group, $R^c$ is a hydrogen atom or a hydroxyl-protecting group, and Ar is an aryl group optionally having a substituent with said metallic reducing agent and a metal having a higher ionization tendency than said metallic reducing agent, giving a 3-hydroxycephem derivative represented by the formula

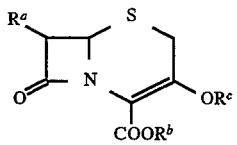

wherein $R^a$, $R^b$ and $R^c$ are as defined above. The starting compound of the formula (F) used in the process is different from the starting compound used in the present invention although they have the same lactam skeleton, because the nitrogen atom of said skeleton is substituted at different positions between the two compounds. Further, the publication does not set forth the use of a specific organohalogen compound at all.

Moreover, when the allenyl-β-lactam compound represented by the formula (1) is reacted with the metallic reducing agent taught in Japanese Unexamined Patent Publication No.211055/1992, merely a 2-exo-methylene penam derivative can be produced (Japanese Unexamined Patent Publication No.97864/1993), that is to say, the 3-substituted cephem derivative contemplated in the present invention can not be obtained.

DISCLOSURE OF THE INVENTION

An object of the present invention is to provide a novel process for preparing a 3-substituted cephem compound having a wide antibacterial spectrum by an expedient reaction procedure under commercially easily implemented conditions, using, as a starting material, an allenyl-β-lactam compound which can be easily produced from an inexpensive penicillin compound by a simple reaction procedure.

According to the present invention, there is provided a process for preparing a 3-substituted cephem compound represented by the formula (3)

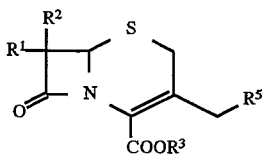

wherein $R^1$, $R^2$ and $R^3$ are as defined above and $R^5$ is a 1-alkenyl group optionally having a substituent or an aryl group optionally having a substituent, the process comprising reacting an allenyl-β-lactam compound represented by the formula

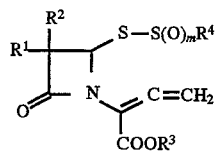

wherein $R^1$, $R^2$, $R^3$, $R^4$ and m are as defined above with an organohalogen compound represented by the formula $$R^5CH_2X \qquad (2)$$

wherein $R^5$ is as defined above and X is a halogen atom in the presence of a metal having a standard oxidation-reduction potential of −0.3 (V/SCE) or less in an amount at least equimolar with the compound of the formula (1) and 0.0001 to 0.5 mole, per mole of the compound of the formula (1), of a metal compound having a higher standard oxidation-reduction potential than said metal.

Given below are specific examples of the groups referred to in the specification. Unless specifically indicated, the halogen atom includes, for example, fluorine, chlorine, bromine, iodine, etc.; the lower alkyl group includes, for example, straight- or branched-chain alkyl groups having 1 to 4 carbon atoms such as methyl, ethyl, n-propyl, isopropyl, n-butyl, isobutyl, sec-butyl, tert-butyl, etc.; and the aryl group includes, for example, phenyl, naphthyl, etc.

Examples of the protected amino group represented by $R^1$ are phenoxyacetamide, p-methylphenoxyacetamide, p-methoxyphenoxyacetamide, p-chlorophenoxyacetamide, p-bromophenoxyacetamide, phenylacetamide, p-methylphenylacetamide, p-methoxyphenylacetamide, p-chlorophenylacetamide, p-bromophenylacetamide, phenylmonochloroacetamide, phenyldichloroacetamide, phenylhydroxyacetamide, phenylacetoxyacetamide, oxophenylacetamide, thienylacetamide, benzamide, p-methylbenzamide, p-tert-butylbenzamide, p-methoxybenzamide, p-chlorobenzamide, p-methoxybenzamide, p-chlorobenzamide, p-bromobenzamide, the groups described in Theodore W. Greene, "Protective Groups in Organic Synthesis", 1981 (hereinafter referred to simply as "literature"), Chapter 7 (pp 218–287), phenylglycylamide, amino-protected phenylglycylamide, p-hydroxyphenylglycylamide, amino- or hydroxyl-protected or both groups-protected p-hydroxyphenylglycylamide, etc. Examples of the groups for protecting the amino group of phenylglycylamide and p-hydroxyphenylglycylamide include the groups set forth in Chapter 7 of the literature (pp 218–287). Examples of the groups for protecting the hydroxyl group of p-hydroxyphenylglycylamide include the groups set forth in Chapter 2 of the literature (pp 10–72).

Examples of the lower alkoxy group represented by $R^2$ are straight- or branched-chain alkoxy groups having 1 to 4 carbon atoms such as methoxy, ethoxy, n-propoxy, isopropoxy, n-butoxy, isobutoxy, sec-butoxy, tert-butoxy, etc.

Examples of the lower acyl group represented by $R^2$ are straight- or branched-chain acyl groups having 1 to 4 carbon atoms such as formyl, acetyl, propionyl, butyryl, isobutyryl, etc.

Examples of the protected hydroxyl group of the lower alkyl group having a hydroxyl group or protected hydroxyl group as a substituent and represented by $R^2$, and examples of the protective group for the protected hydroxyl group represented by $R^2$ include the groups set out in Chapter 2 of the literature (pp 10 to 72). The substituted lower alkyl group represented by $R^2$ may be a group wherein one or more hydrogen atoms are substituted on the same or different carbon atoms by the same or different substituents selected from the hydroxyl group and protected hydroxyl group.

Examples of the carboxylic acid-protecting group represented by $R^3$ are benzyl, p-methoxybenzyl, p-nitrobenzyl, diphenylmethyl, trichloroethyl, tert-butyl and the groups set out in Chapter 5 of the literature (pp 152 to 192).

Examples of the nitrogen-containing aromatic heterocyclic group of the nitrogen-containing aromatic heterocyclic group optionally having a substituent and represented by $R^4$ are thiazole-2-yl, thiadiazole-2-yl, benzothiazole-2-yl, oxazole-2-yl, benzooxazole-2-yl, imidazole-2-yl, benzoimidazole-2-yl, pyrimidinyl, pyridyl, etc.

Examples of the substituent which may be possessed by the aryl group or nitrogen-containing aromatic heterocyclic group represented by $R^4$ are halogen, hydroxyl, nitro, cyano, aryl, lower alkyl, amino, mono-lower alkylamino, di-lower alkylamino, mercapto, alkylthio or arylthio group represented by $R^6S$— ($R^6$ is a lower alkyl group or aryl group), formyloxy, acyloxy represented by $R^6COO$— ($R^6$ is as defined above), formyl, acyl represented by $R^6CO$— ($R^6$ is as defined above), alkoxy or aryloxy represented by $R^6O$— ($R^6$ is as defined above), carboxyl, alkoxycarbonyl or aryloxycarbonyl represented by $R^6OCO$— ($R^6$ is as defined above), etc. The aryl group or nitrogen-containing aromatic heterocyclic group represented by $R^4$ may be a group wherein one or more hydrogen atoms are substituted by one or more and the same or different substituents selected from said substituents.

Examples of the substituent which may be possessed by the 1-alkenyl or aryl group represented by $R^5$ include the substituents exemplified above for the groups $R^4$. The 1-alkenyl or aryl group represented by $R^5$ may be a group wherein one or more hydrogen atoms may be substituted on one or more and the same or different carbon atoms by one or more and the same or different substituents selected from said substituents.

The allenyl-β-lactam compound of the formula (1) to be used as the starting material in the present invention is a known compound and can be easily prepared, for example, by methods disclosed in Torii et al, Synlett, p 888 (1991) and Japanese Unexamined Patent Publication No.282359/1992.

According to the present invention, the 3-substituted cephem compound of the formula (3) can be prepared by reacting the allenyl-β-lactam compound of the formula (1) with the organohalogen compound of the formula (2) in the presence of at least an equimolar amount, relative to the compound of the formula (1), of the metal having a standard oxidation-reduction potential of −0.3 (V/SCE) or less and 0.0001 to 0.5 mole, per mole of the compound of the formula (1), of the metal compound having a higher standard oxidation-reduction potential than said metal.

It is essential in the invention to use the organohalogen compound of the formula (2). Even if a compound which is analogous to, but different from, the organohalogen compound of the formula (2) such as a halogenated alkenyl is used in place of the organohalogen compound of the formula (2), the contemplated compound of the present invention can not be obtained as described in Comparative Example 1.

The amount of the organohalogen compound of the formula (2) used is 1 to 3 moles, preferably 1 to 2 moles, per mole of the compound of the formula (1).

Examples of the metal having a standard oxidation-reduction potential of −0.3 (V/SCE) or less are magnesium, aluminum, zinc, iron, nickel, tin, lead, etc. Among them, magnesium, aluminum, zinc and tin are preferred. The form of these metals is not specifically limited and may be suitably selected from a wide range including powders, plates, foils, masses, needles, etc. Preferred are powders and foils. The particle size of the particulate metal can be suitably selected from a wide range and is preferably in the range of about 10 to about 300 mesh. The amount of the metal used is about 1 to about 50 moles, preferably about 1 to about 10 moles, per mole of the compound of the formula Examples of the metal compound having a higher standard oxidation-reduction potential than said metal include lead compounds such as lead fluoride, lead chloride, lead bromide, lead iodide and like halogenated lead, lead nitrate, lead sulfate, lead perchlorate, lead borate, lead carbonate, lead phosphate and like inorganic salts of lead, lead acetate, lead oxalate, lead stearate and like fatty acids of lead, lead oxide, lead hydroxide, etc., copper compounds such as copper fluoride, copper chloride, copper bromide, copper iodide and like halogenated copper, copper nitrate, copper sulfate, copper perchlorate and like inorganic salts of copper, copper acetate, copper oxalate and like fatty acids of copper, etc., titanium compounds such as titanium fluoride, titanium chloride, titanium bromide, titanium iodide and like halogenated titanium, titanium sulfate, titanium nitrate and like inorganic salts of titanium, etc., bismuth compounds such as bismuth fluoride, bismuth chloride, bismuth iodide and like halogenated bismuth, bismuth nitrate, bismuth sulfate and like inorganic salts of bismuth, bismuth oxide, etc., antimony compounds such as antimony fluoride, antimony chloride, antimony bromide, antimony iodide and like halogenated antimony, antimony sulfate and like inorganic salts of antimony, antimony oxide, etc., nickel compounds such as nickel fluoride, nickel chloride, nickel bromide, nickel iodide and like halogenated nickel, nickel acetate and like fatty acids of nickel, nickel nitrate, nickel sulfate, nickel perchlorate and like inorganic salts of nickel, tetrachloronickel (II) acid tetraethylammonium, tetrabromonickel (II) acid tetraethylammonium, hexaamminenickel (II) chloride, dinitrotetraamminenickel (II), tris(ethylenediamine)nickel (II) sulfate, ethylenediaminetetraaquanickel (II) sulfate-hydrate, dinitrobis(ethylenediamine)nickel (II), bis(N,N-dimethylethylenediamine)nickel (II) perchlorate and like inorganic complexes of nickel, dichloro(bipyridyl)nickel (II), chloro(η-cyclopentadienyl)(triphenylphosphine)nickel (II), diclorobis(triphenylphosphine)nickel (II), dibromobis (triphenylphosphine)nickel (II), dichlorobis {1,1'bis (diphenylphosphino)ferrocene}nickel (II) and like organic complexes of nickel (II), tetrakis(triphenylphosphine)nickel (0), tris(triphenylphosphine)nickel (0), nickel (0) acetylacetonato, nickel (0) hexafluoroacetylacetonato and like organic complexes of nickel (0), etc. Among these metal compounds, nickel compounds are preferred. These metal compounds may be used singly or in combination. The yield of the contemplated compound obtainable by the reaction is increased by conjoint use of a nickel compound with at least one of other metal compounds, preferably with a lead compound or with a lead compound and at least one of other metal compounds.

The amount of a single metal compound used is 0.0001 to 0.5 mole, preferably 0.001 to 0.4 mole, per mole of the compound of the formula (1). For example, if two different metal compounds are used as selected from the above metal compounds, each of the two compounds is used in the aforesaid amount. The metal having a standard oxidation-reduction potential of −0.3 (V/SCE) or less and the metal compound having a higher standard oxidation-reduction potential than said metal can be used in various combinations. Specific examples of the combinations are Al/Pb compounds, Al/Bi compounds, Zn/Pb compounds, Zn/Bi compounds, Mg/Bi compounds, Mg/Cu compounds, Sn/Ti compounds, Sn/Bi compounds, Sn/Sb compounds, etc., preferably Al/Pb compounds-Ni compound, Zn/Pb compounds-Ni compound.

Examples of solvents which can be used in the invention are amides such as dimethylacetamide, dimethylformamide, 1-methyl-2-pyrrolidinone, hexamethylphosphoric triamide, etc., nitriles such as acetonitrile, propionitrile, butyronitrile, isobutyronitrile, valeronitrile, etc., dimethyl sulfoxide, etc. These solvents can be used singly or in mixture with each other or with other conventional solvents. Examples of such conventional solvents are methyl formate, ethyl formate, propyl formate, butyl formate, methyl acetate, ethyl acetate, propyl acetate, butyl acetate, methyl propionate, ethyl propionate and like lower alkyl esters of lower carboxylic acids, diethyl ether, ethyl propyl ether, ethyl butyl ether, dipropyl ether, diisopropyl ether, dibutyl ether, methyl cellosolve, dimethoxyethane and like ethers, tetrahydrofuran, dioxane and like cyclic ethers, benzene, toluene, xylene, chlorobenzene, anisole and like substituted or unsubstituted aromatic hydrocarbons, pentane, hexane, heptane, octane and like hydrocarbons, cyclopentane, cyclohexane, cycloheptane, cyclooctane and like cycloalkanes, dichloromethane, chloroform, dichloroethane, trichloroethane, dibromoethane, propylene dichloride, carbon tetrachloride, Freon (trademark) and like halogenated hydrocarbons, etc. Among them, preferable are mixtures predominantly containing dimethylformamide, 1-methyl-2-pyrrolidinone, dimethyl sulfoxide or the like. The amount of the solvent used is about 0.5 to about 200 l, preferably 0 to about 50 l, per kg of the compound of the formula (1).

The reaction is conducted at a temperature of −10° to 80° C., preferably 0° to 50° C. The reaction can favorably proceed even at around room temperature.

The compound of the formula (3) produced by the reaction of the present invention can be purified by a conventional procedure such as extraction or recrystallization after completion of the reaction to give a substantially pure product. The reaction product, of course, can be purified by other methods.

According to the process of the invention, the contemplated cephem compound of the formula (3) can be prepared at an ambient temperature (room temperature) without necessitating a harmful tin compound. The cephem compound obtained in the invention has a wide antibacterial spectrum and is of high utility.

BEST MODE TO CARRY OUT THE INVENTION

The following Examples and Comparative Example are presented to illustrate the invention in more detail.

Example 1

Mixed together were 100 mg of the compound of the formula (1) wherein $R^1$ is phenylacetamide, $R^2$ is a hydrogen atom, $R^3$ is p-methoxybenzyl, $R^4$ is phenyl, and m is 2 (hereinafter referred to as "compound (1a)"), 4.9 mg of dichloro(bipyridyl) nickel (II), 3.2 mg of lead bromide, 23 mg of finely divided aluminum foil and 3 ml of 1-methyl-2-pyrrolidinone. Thirty μl of allyl bromide was added and the mixture was subjected to reaction at room temperature with stirring. The resulting reaction mixture was extracted with ethyl acetate and 5% hydrochloric acid. The organic layer was washed with water and an aqueous solution of sodium chloride, and dried over sodium sulfate. The solvent was distilled off at reduced pressure. The obtained concentrated residue was purified with a silica gel column (benzene/ethyl acetate=8/1), giving 75 mg of the compound of the formula (3) wherein $R^1$ is phenylacetamide, $R^2$ is a hydrogen atom, $R^3$ is p-methoxybenzyl and $R^5$ is vinyl (hereinafter referred to as "compound (3a)") (yield 90%). The obtained compound was identical in NMR spectrum data with an authentic sample prepared independently.

Example 2

The same reaction as in Example 1 was performed with the exception of using the finely divided aluminum foil in an amount reduced from 23 mg to 12 mg, whereby the compound (3a) was produced in a yield of 88%.

Example 3

The compound 3(a) was obtained in a yield of 57% by the same reaction as in Example 1 with the exception of not using dichloro(bipyridyl)nickel (II).

Example 4

The same reaction as in Example 1 was carried out with the exception of using N,N-dimethylformamide in place of 1-methyl-2-pyrrolidinone, whereby the compound (3a) was produced in a yield of 77%.

Example 5

The same reaction as in Example 1 was carried out with the exception of using nickel chloride in place of dichloro (bipyridyl)nickel (II), whereby the compound (3a) was produced in a yield of 67%.

Example 6

The same reaction as in Example 1 was carried out with the exception of using powdery zinc in place of finely divided aluminum foil, whereby the compound (3a) was produced in a yield of 82%.

Examples 7 to 15

The same reaction as in Example 1 was conducted using the compound (1a) and the compound of the formula (2) having the substituent of $R^5$ as shown below in Table 1, giving the corresponding compound of the formula (3) wherein $R^1$ is phenylacetamide, $R^2$ is a hydrogen atom, $R^3$ is p-methoxybenzyl and $R^5$ is as shown in Table 1.

TABLE 1

| | $R^5CH_2X$ | | | |
|---|---|---|---|---|
| Example | $R^5$ | X | Yield of comp. (3) | |
| 7 | Vinyl | Cl | 89% | 3a |
| 8 | Vinyl | I | 76% | 3a |
| 9 | 1-Methylvinyl | Cl | 78% | 3b |
| 10 | 1-Propenyl | Br | 81% | 3c |
| 11 | Styryl | Br | 74% | 3d |
| 12 | Styryl | Br | 84% | 3d |
| 13 | 2-Methyl-1-propenyl | Br | 85% | 3e |
| 14 | 2-Methyl-1-propenyl | Cl | 81% | 3e |
| 15 | 2-Bromovinyl | Br | 81% | 3f |

Example 16

There were weighed out 100 mg of the compound (1a), 5 mg of dichloro(bipyridyl)nickel (II), 6.3 mg of lead bromide and 9 mg of finely divided aluminum foil, and 1 ml of 1-methyl-2-pyrrolidinone was added. Forty one μl of benzyl bromide was added, and the mixture was subjected to reaction at room temperature with stirring. The obtained reaction mixture was extracted with ethyl acetate and 5% hydrochloric acid. The organic layer was washed with water and an aqueous solution of sodium chloride, and dried over sodium sulfate. The solvent was distilled off at reduced pressure. The obtained concentrated residue was purified with a silica gel column (benzene/ethyl acetate=8/1), giving 83 mg of the compound of the formula (3) wherein $R^1$ is phenylacetamide, $R^2$ is a hydrogen atom, $R^3$ is p-methoxybenzyl and $R^5$ is phenyl (hereinafter referred to as "compound (3g)") (yield 91%). The obtained compound was identical in NMR spectrum data with an authentic sample prepared independently.

Examples 17 to 20

The same reaction as in Example 16 was carried out using the compound (1a) and the compound of the formula (2) having the substituent of $R^5$ as shown below in Table 2, giving the corresponding compound of the formula (3) wherein $R^1$ is phenylacetamide, $R^2$ is a hydrogen atom, $R^3$ is p-methoxybenzyl and $R^5$ is as shown below in Table 2.

TABLE 2

| | $R^5CH_2X$ | | | |
|---|---|---|---|---|
| Example | $R^5$ | X | Yield of comp. (3) | |
| 17 | Phenyl | Cl | 80% | 3g |
| 18 | p-Bromophenyl | Br | 86% | 3h |
| 19 | p-Tolyl | Br | 82% | 3i |
| 20 | P-Methoxyphenyl | Cl | 78% | 3j |

Examples 21 to 25

The same reaction as in Example 16 was carried out except that the compound of the formula (1) wherein $R^1$ is phenylacetamide, $R^2$ is a hydrogen atom, $R^3$ is diphenylmethyl, $R^4$ is phenyl, and m is 2 (hereinafter referred to as "compound (1b)") was used in place of the compound (1a), giving the corresponding compound of the formula (3) wherein $R^1$ is phenylacetamide, $R^2$ is a hydrogen atom, $R^3$ is diphenylmethyl and $R^5$ is as shown below in Table 3.

TABLE 3

| | $R^5CH_2X$ | | |
|---|---|---|---|
| Example | $R^5$ | X | Comp. (3) |
| 21 | Vinyl | Br | 3k |
| 22 | 1-Propenyl | Br | 3l |
| 23 | 2-Methyl-1-propenyl | Br | 3m |
| 24 | P-Tolyl | Br | 3n |
| 25 | P-Methoxyphenyl | Cl | 3o |

Examples 26 to 30

The same reaction as in Example 16 was carried out except that the compound of the formula (1) wherein $R^1$ is phenylacetamide, $R^2$ is a hydrogen atom, $R^3$ is p-methoxybenzyl, $R^4$ is 2-benzothiazolyl, and m is 0 (hereinafter referred to as "compound (1c)") was used in place of the compound (1a), giving the corresponding compound of the formula (3) wherein $R^1$ is phenylacetamide, $R^2$ is a hydrogen atom, $R^3$ is p-methoxybenzyl and $R^5$ is as shown below in Table 4.

TABLE 4

| | $R^5CH_2X$ | | |
|---|---|---|---|
| Example | $R^5$ | X | Comp. (3) |
| 26 | Vinyl | Br | 3a |
| 27 | 1-Propenyl | Br | 3c |
| 28 | 2-Methyl-1-propenyl | Br | 3e |
| 29 | p-Tolyl | Br | 3i |
| 30 | P-Methoxyphenyl | Cl | 3j |

Comparative Example 1

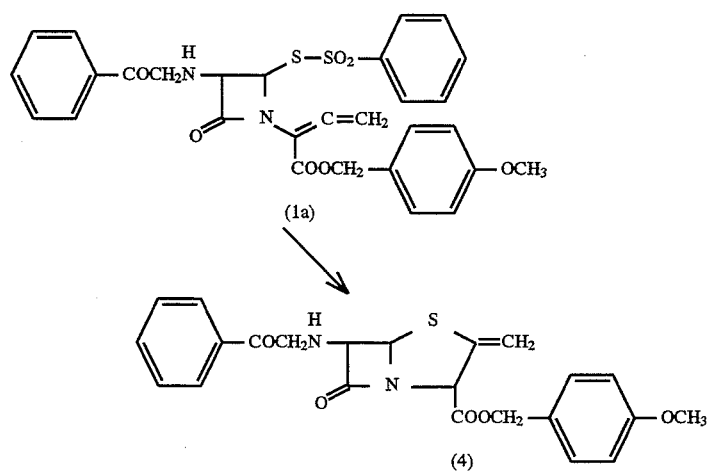

The same procedure as Example 1 was carried out except that 1-propenyl bromide was used in place of allyl bromide, whereby 60% of compound (1a) was recovered and 30% of 2-exomethylenepenam represented by the formula (4) were obtained, but the contemplated compound (3a) was not produced.

What we claim is:

1. A process for preparing a 3-substituted cephem compound of the formula

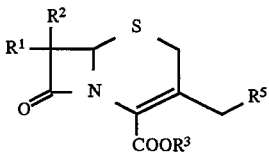

wherein $R^1$ is a hydrogen atom, a halogen atom, an amino group or a protected amino group, $R^2$ is a hydrogen atom, a halogen atom, a lower alkoxy group, a lower acyl group, a lower alkyl group, a lower alkyl group having a hydroxyl group or a protected hydroxyl group as a substituent, a hydroxyl group or a protected hydroxyl group, $R^3$ is a hydrogen atom, or a carboxylic acid-protecting group, and $R^5$ is a 1-alkenyl group optionally having a substituent or an aryl group optionally having a substituent, which comprises reacting a) an allenyl-β-lactam compound represented by the formula

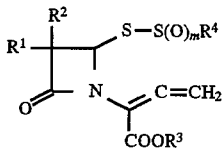

wherein $R^1$, $R^2$ and $R^3$ are as defined above, $R^4$ is an aryl group optionally having a substituent or a nitrogen-containing aromatic heterocyclic group optionally having a substituent, and m is 0 or 2;

with b) an organohalogen compound represented by the formula

$R^5CH_2X$ wherein $R^5$ is as defined above and X is a halogen atom;

in the presence of c) a metal having a standard oxidation-reduction potential not higher than −0.3 (V/SCE) in an amount at least equimolar with the allenyl-β-lactam compound a); and 0.0001 to 0.5 mole, per mole of the allenyl-β-lactam compound a), of a metal compound d) having a higher standard oxidation-reduction potential than the metal (c).

2. A process according to claim 1, wherein the metal having a standard oxidation-reduction potential not higher than −0.3 (V/SCE) is at least one member selected from the group consisting of magnesium, aluminum, nickel, zinc, iron, tin and lead.

3. A process according to claim 1, wherein the metal having a standard oxidation-reduction potential not higher than −0.3 (V/SCE) is at least one member selected from the group consisting of magnesium, aluminum, zinc and tin.

4. A process according to claim 1, wherein the metal compound having a higher standard oxidation-reduction potential than said metal having a standard oxidation-reduction potential not higher than −0.3 (V/SCE) is a nickel compound.

5. A process according to claim 1, wherein 0.0001 to 0.5 mole of the metal compound having a higher standard oxidation-reduction potential than said metal having a standard oxidation-reduction potential not higher than −0.3 (V/SCE) is used per mole of the allenyl-β-lactam compound.

6. A process according to claim 1 wherein a nickel compound is used along with at least one of other metal compounds having a higher standard oxidation-reduction potential than said metal having a standard oxidation-reduction potential of −0.3 (V/SCE) or less.

7. A process according to claim 1 wherein a nickel compound is used along with a lead compound.

* * * * *

UNITED STATES PATENT AND TRADEMARK OFFICE
CERTIFICATE OF CORRECTION

PATENT NO.: 5,656,755
DATED : August 12, 1997
INVENTOR(S): TORI et al.

It is certified that error appears in the above-identified patent and that said Letters Patent is hereby corrected as shown below:

On the title page of the patent item [54], the Title, is incorrect in that "PROCESS FOR PREPARATION ON 3-SUBSTITUTED CEPHEM COMPOUND" should be --PROCESS FOR PREPARATION OF 3-SUBSTITUTED CEPHEM COMPOUND--.

On the title page of the patent item [30], the Foreign Application Priority Data, is also incorrect in that the date is in error. Please delete "September 11, 1993" and add --November 9, 1993-- therefor.

Signed and Sealed this

Sixteenth Day of December, 1997

Attest:

BRUCE LEHMAN

Attesting Officer

Commissioner of Patents and Trademarks